United States Patent [19]

Wilkinson et al.

[11] 4,407,777
[45] Oct. 4, 1983

[54] BLOOD OXYGENATOR

[76] Inventors: William R. Wilkinson, 16422 Quail Park, Missouri City, Tex. 77489; Richard F. Wilkinson, Sr., 2114 S. Grand Ave., Santa Anna, Calif. 92705

[21] Appl. No.: 285,797

[22] Filed: Jul. 22, 1981

[51] Int. Cl.³ .............................................. A61M 1/03
[52] U.S. Cl. ................................ 422/46; 128/DIG. 3; 261/DIG. 28; 422/47
[58] Field of Search ................................... 422/46, 47; 261/DIG. 28; 128/DIG. 3

[56] References Cited

U.S. PATENT DOCUMENTS

| | | |
|---|---|---|
| 3,768,977 | 10/1973 | Brumfield et al. |
| 3,769,162 | 10/1973 | Brumfield |
| 3,807,958 | 4/1974 | Brumfield et al. |
| 3,870,470 | 3/1975 | Yoshida et al. |
| 3,994,689 | 11/1976 | DeWall |
| 4,067,696 | 1/1978 | Curtis ................................... 422/47 |
| 4,138,288 | 2/1979 | Lewin ................................ 422/46 X |
| 4,138,464 | 2/1979 | Lewin ................................... 422/46 |
| 4,254,081 | 3/1981 | Streczyn et al. ..................... 422/46 |
| 4,280,981 | 7/1981 | Harnsberger ......................... 422/46 |

Primary Examiner—Barry S. Richman
Attorney, Agent, or Firm—Vaden, Eickenroht, Thompson, Bednar & Jamison

[57] ABSTRACT

A blood oxygenator for one time use and discard in medical procedures. The blood oxygenator has a unitary transparent sealed vessel with first and second blood treating stages arranged for series flow. The first stage receives an inflow of blood and oxygen and it has integrated oxygenating and heat exchanging elements that include a plurality of vertical ribs and flutes internested to provide upright thin-film blood and oxygen flow channels. These ribs and flutes surround, by a common wall, a heat exchanger with upright channels for counter-directional coolant flow relative to the blood and oxygen flow. The second stage has integrated blood degassing and defoaming elements including a vertical perforated wall surrounded by a porous foam member with a surrounding reservoir of outflowing degassed and defoamed blood and a vent for free oxygen gas.

6 Claims, 6 Drawing Figures

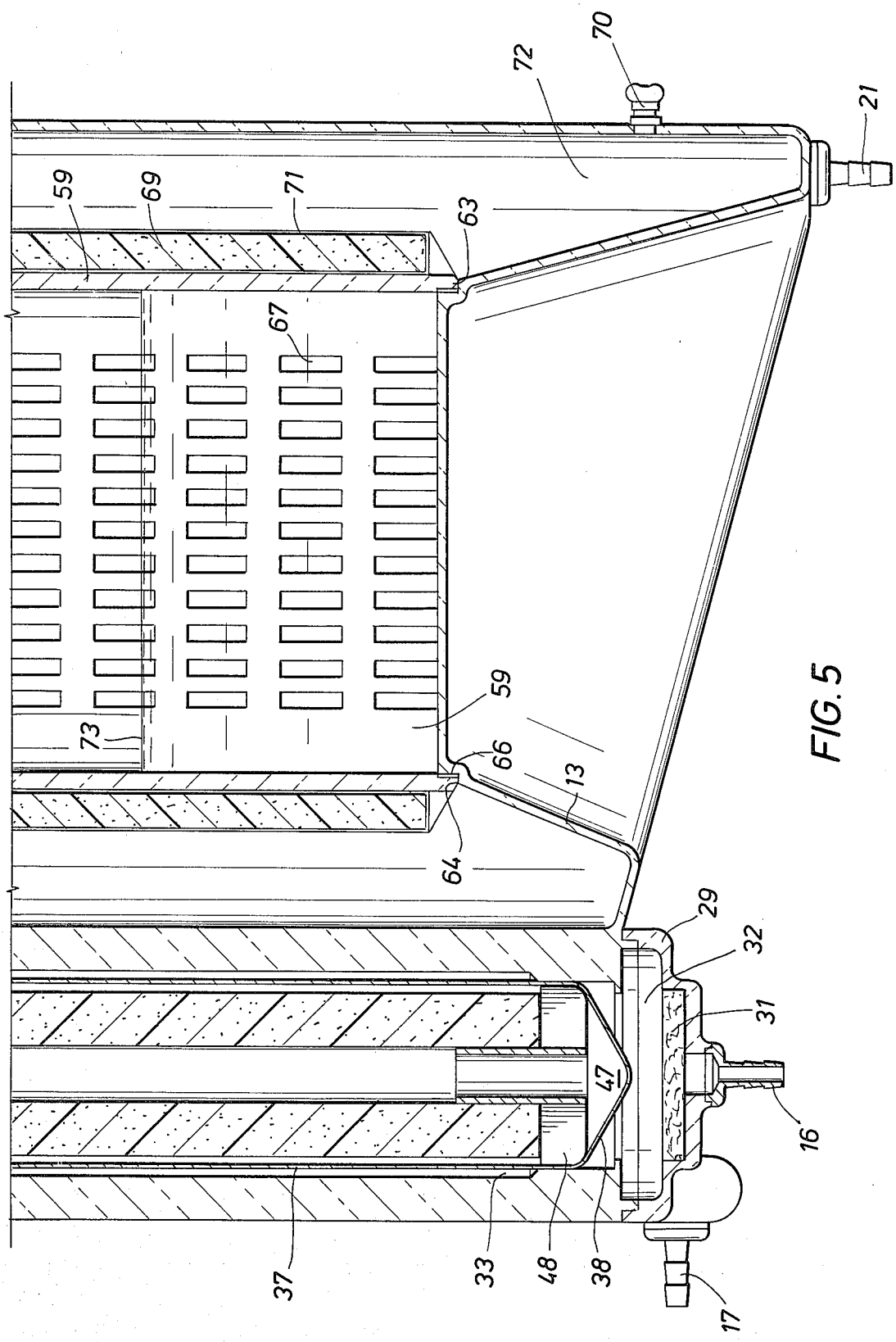

BLOOD OXYGENATOR

BACKGROUND OF THE INVENTION

1. Field of the Invention

This invention relates to the oxygenation and temperature adjustment of blood during medical procedures. More particularly, the invention concerns a disposable, one-use novel blood oxygenator with integrated stages for (1) oxygenating and heat exchanging and (2) defoaming and degassing the blood during treatment.

2. Description of Prior Art

In many medical procedures, the patient during an operation, is subject to blood treatment in a bypass flow outside of his body. The blood treatment includes oxygenation and temperature adjustment in an apparatus that may be termed as a "blood oxygenator".

This device has several important functions which include; (1) cooling the blood in the early portion of an operation, (2) dissolving oxygen into the blood, (3) removing all free oxygen bubbles and foam from the blood before its return to the patient, and (4) warming the blood to heat the patient in the latter portion of the operation so that the surgeon can close the wound.

The cooling and heating of human blood is confined to certain limits which must not be exceeded. For example, the lower temperature limit is where tissue damage occurs by freezing water. The upper temperature limit is 42 degrees centigrade, which limit if exceeded causes degradation of the blood.

In addition, the medical profession has turned increasingly to one-use disposable blood oxygenators which are ready to use in sterile packages since post operative clean-up and sterilization is hazardous if improper but expensive to do correctly.

Disposable blood oxygenators have been made for one-time use and also, fabricated from transparent plastic members so that their functioning is readily verified visually. In addition, the device must be relatively low cost for one time use but yet must perform perfectly in use since a patients well being is at risk of a malfunction.

U.S. Pat. Nos. 3,768,977, 3,769,162, 3,807,958, 4,138,288 and 4,138,464 show blood oxygenators of the prior art. The blood oxygenators shown in these patents have been used by the medical profession but their construction and assembly are complex and therefore expensive. In these devices, the oxygenating and heat exchanging stage is separated from a defoaming and degassing stage.

Attempts have been made to improve the oxygenating and heat exchanging stage as shown in U.S. Pat. Nos. 3,870,470 and 3,994,689. In these patents, this stage is of a design to simplify construction while trying to combine the oxygenating and heat exchanging functions by common wall elements. However, these devices are structurally too large when capable of producing the proper treatment of blood.

The present invention in a blood oxygenator has all of the desired characteristics in a one-use and discard transparent device. The device has a construction permitting an "insert" type of assembly of all operative internal elements into a vessel which is then sealed at the top by a cover that includes the remainder of the elements. In addition, the device is more compact and performs blood treatment as to oxygenating, heat exchanging, degassing and defoaming in a better improved manner than the prior art blood oxygenators.

SUMMARY OF THE INVENTION

In accordance with this invention, there is provided a blood oxygenator with an enclosed and sealed vessel containing first and second stages arranged in series flow in blood treatment. The first stage has inlets of inflowing streams of blood and oxygen gas through integrated oxygenating and heat exchanging elements. These elements include vertical ribs and flutes internested to define a plurality of upright, thin-film blood and oxygen flow channels surrounding a heat exchanger with upright channels for coolant flow provided by a wall common to the flutes. The second stage receives a mixture of blood and gas from the first stage and includes degassing and defoaming elements from providing in outlets separate outflows of free oxygen gas and a bubble and foam free temperature adjusted oxygenated blood.

In a specific embodiment, the second stage is a vertical perforated elliptical wall carrying exterior ribs on which is mounted at a fixed distance an open-pore foam member with a blood reservoir surrounding the foam member. The foam member may be enclosed sideways by a woven cover formed of synthetic polymeric threads. Passage of the blood laterally from the vertical perforated wall through the foam and woven cover provides a defoamed and degassed blood that can be safely returned to the patient.

DESCRIPTION OF THE DRAWINGS

FIG. 5 is a partial vertical section of the lower portion of the device shown in FIG. 1; and FIG. 6 is a partial cross section through the upper portion of the device of FIG. 4 and taken along line 6—6.

In the drawings, the several embodiments of the device have common elements of construction. In regard to the several figures, like elements carry like numerals to simplify description of these embodiments of the present device.

DESCRIPTION OF PREFERRED EMBODIMENTS

Figure 1:
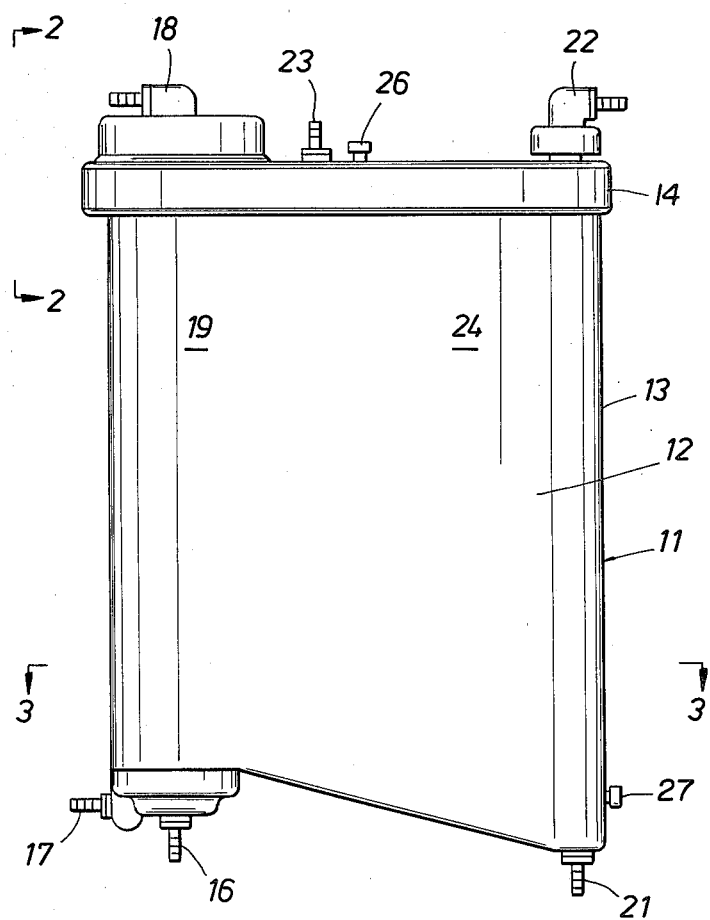
FIG. 1 is a perspective view of a blood oxygenator arranged according to the present invention.

Referring to FIG. 1, there is shown a blood oxygenating device 11 which is constructed in accordance with the present invention. The device 11 has a unitary enclosed and sealed vessel 12 formed of an open top lower container 13 which is sealed fluid tight by an enclosing cover 14 in final assembly. Although the vessel 12 may be formed of any suitable material, it is preferred to mold the cover and container from a transparent thermoplastic such as an acrylic polymer.

The vessel 12 is provided with an oxygen gas inlet 16 and a blood inlet 17 to which inlets are connected hoses in a conventional manner. A coolant inlet/outlet head 18 is carried by the cover 14. The inlets 16 and 17 and head 18 are associated with the first stage 19 which includes the oxygenating and heat exchanging elements.

The vessel is also provided with a defoamed and degassed temperature adjusted blood outlet 21 in the container 13 and free oxygen gas outlet head 22 in the cover. The outlet 21 and head 22 connect to the customary hoses in the known manner. If desired, the cover 12 may also carry an inlet 23 for priming the second stage 24 with IV fluid at the beginning of the blood treatment. Several auxiliary ports 26 and 27 may also be provided the second stage 24. In the second stage 24, the outlets 21 and 22 are associated with the defoaming and degassing elements therein.

Figure 3:
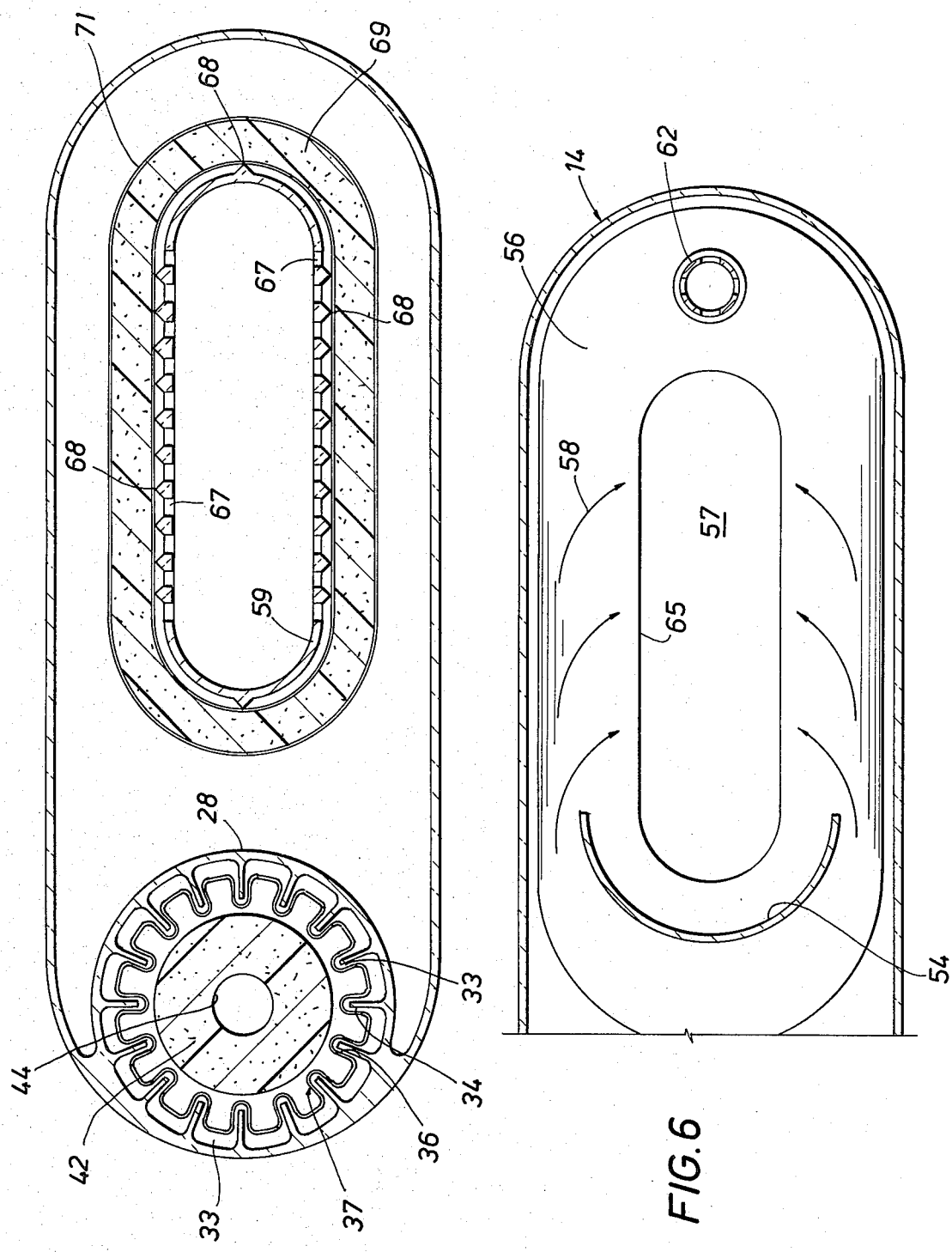
FIG. 3 is a cross section along line 3—3 of the device in FIG. 1 showing the construction of the first and second stages.
Figure 4:
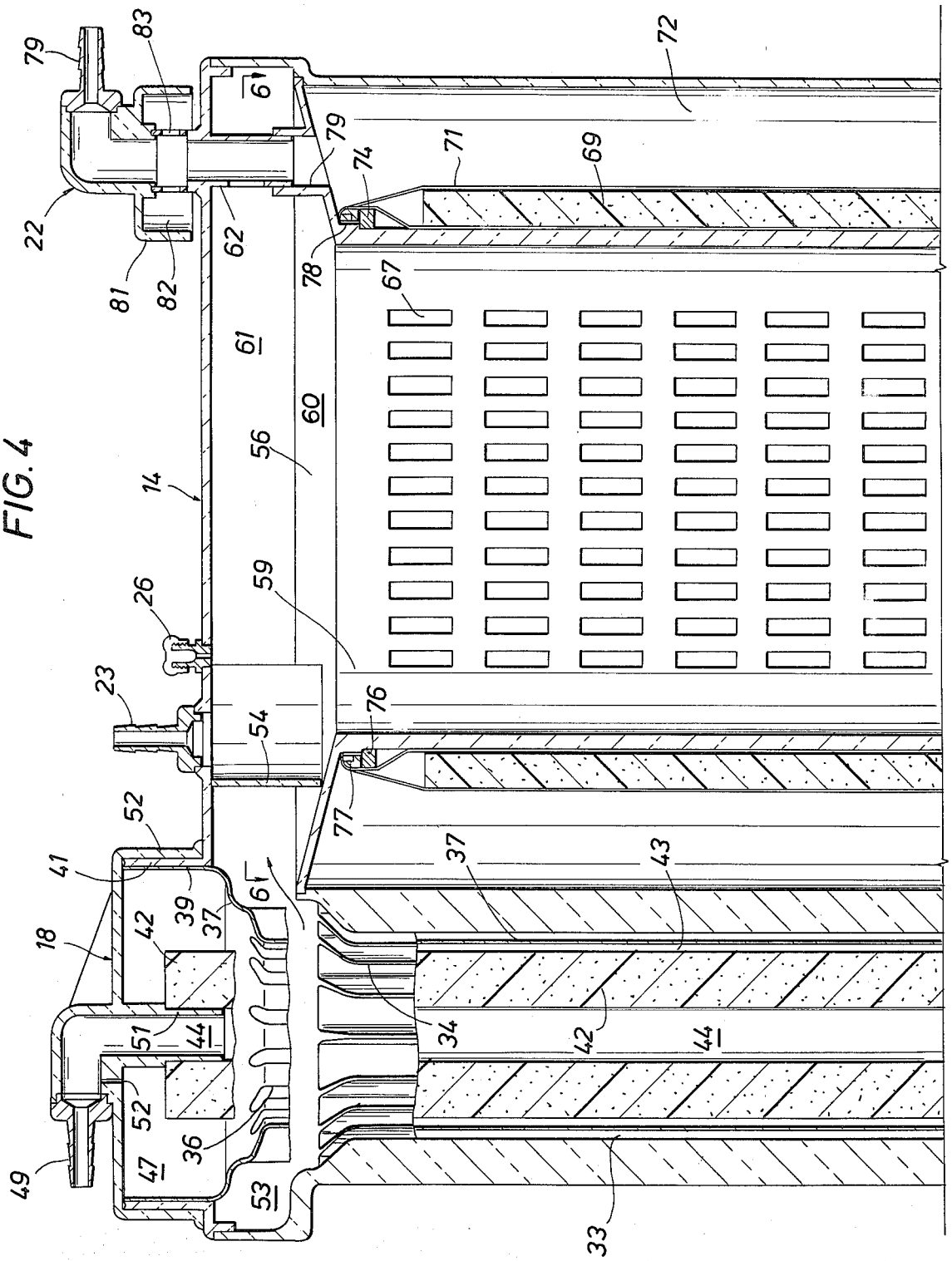
FIG. 4 is a partial vertical section of the upper portion of the device shown in FIG. 1.

The container 13 in the first stage 19 is provided with a full height integral upright cylindrical wall 28, which construction is best seen in FIGS. 3–5. The lower end of the wall 28 is sealed by a cap 29 which carries the inlets 16 and 17. A porous diffuser 31 may be placed into the cap 29 to insure a fine dispersion of oxygen gas into the inflowing blood in the inlet chamber 32 of the oxygenating and heat exchanging stage 19.

The blood and oxygen gas flow upwardly in the wall 28 through a plurality of vertical thin-film flow channels 33. These channels are of small dimension and insure that the blood and oxygen gas mixture flows in a "plug" flow so that no stagnant blood regions can form. In addition, the thin-film flow promotes dissolving of the oxygen gas into the blood while enhancing the indirect heat exchange function relative to coolant flow.

Preferably these thin film flow channels are formed by vertical inward facing ribs 34 formed integrally in the molded wall 28. These ribs 34 cooperate with flutes 36 which are outwardly directed but vertically oriented and carried on a heat exchanger tube 37. The tube 37 is best made of metal (e.g., aluminum) and the longitudinal flutes 36 provided by mandrel drawing or other manufacturing techniques. The tube 37 has a closed bottom 38 and its flutes 36 are internested with the ribs 34 to form the thin-film flow channels 33. The lateral clearance between the ribs and flutes is not great and usually good results are obtained at a clearance of one hundred thousandth of an inch in which will pass upwardly flowing blood and oxygen gas. The bottom 38 usually is conical for better fluid distribution into the channels 33 from the chamber 32.

The upper portion of the tube 37 has an outwardly flared flange 39 which is secured with a neck 41 formed in the cover 14 by the coolant head 18. The tube 37 slides longitudinally downwardly into the wall 28 and into its mounted position in the container 14.

Figure 2:
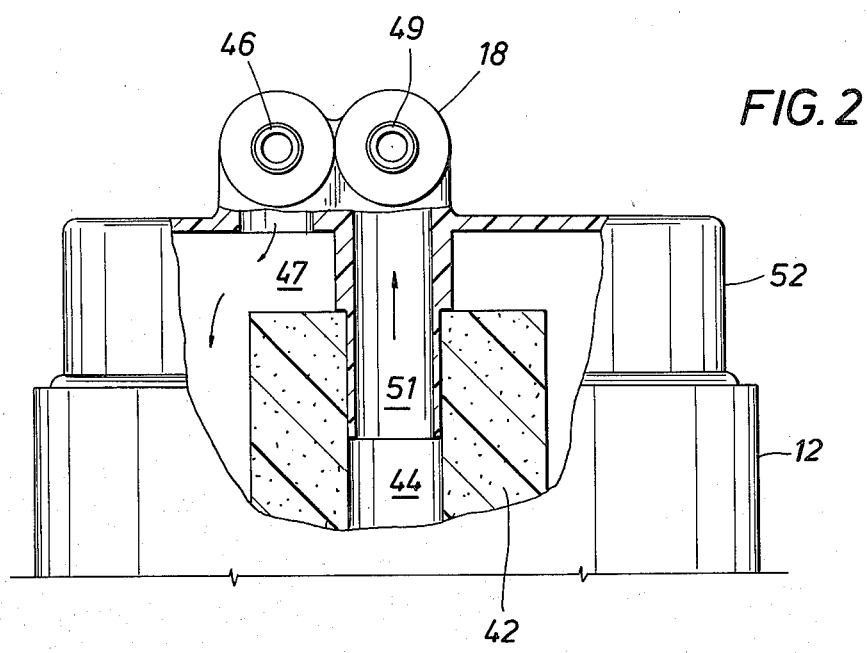
FIG. 2 is a partial section along line 2—2 of the device of FIG. 1 illustrating coolant inlet/outlet features.

An insulative tubular member 42 (e.g., closed pore styrofoam) is mounted coaxially within the tube 37 and spaced therefrom by an annulus 43. An axial passageway 44 extends centrally through the member 42. The member 42 slides longitudinally downwardly into the tube 37. As seen in FIGS. 2 and 4, the head 18 has a coolant inlet 46 opening into the chamber 47 which leads into the annulus 43. As a result, the inflowing coolant traverses counterdirectionally along the inner surface of the tube 37 that is a common wall between these flows. This common wall is an important asset in the first stage 19 in that at no time can the blood exceed the temperature of the coolant, and especially 42 degrees centigrade.

The coolant flows downwardly from the annulus 43 through a spacer spider 48 across the bottom 38 of the tube 37. Now, the coolant flows upwardly through the passageway 44 to an outlet 49 for coolant outflow. The head 18 carries a stepped outlet pipe 51 which secures the member 42 at its upper end as does the spinder 48 at its lower end. The head 18 has a rim 52 which is secured fluid tightly about the neck 50 so that the coolant flows are captive in the first stage 19.

A bypass vent 52 is provided between the coolant inflow chamber 47 and the outlet 49 in the head 18. Any gas that enters the chamber 47 will be quickly asperated into the outflowing coolant at the outlet 49. As an important result, the coolant in the chamber 47 and downflowing the annulus 43 is liquid and no gas pocket bubbles or slugs can rest or pass into the annulus 43 to interfere with the coolant function during heat exchange with the upflowing blood across the tube 37.

The blood and oxygen gas flowing upwardly leave the channels 33 into an annulus outlet chamber 53 that directs flow into the second stage 24 as can be seen in FIG. 4. The blood and gas flow divides horizontally about an upright semi-cylindrical flow diverter 54 (as best seen in FIG. 6) and then it enters as indicated by arrows 58 a conical inlet member 56 into a central opening 57 formed within an elliptical or oblong vertical perforated wall 59. The member 56 is arranged on the cover 14 with the conical surface ending at the inner surface 65 of wall 59 whereby the incoming blood and gas flow passes downwardly along such inner surface in a relatively slash-free flow. A large portion of the oxygen gas is disengaged from the blood upon the member 56 and passes along the gas outlet chamber 61 into the gas head 22 through a slotted outlet tube 62.

The wall 59 is inserted downwardly into container 13 and seated at its bottom end 63 upon a complementary oblong ring 64 formed in the bottom of the container 13. A seal 66 may seal fluid tight the wall to the ring 64.

The open end 60 of the wall 59 can be connected or molded integral with the conical member 56. The wall 59 has a plurality of vertically elongated openings 67 between a plurality of vertical exterior ribs 68. The relatively gas free blood flows laterally outwardly through these openings, and passes through an openpore foam member 69 which rests upon ribs 68 and encloses the wall 59. Preferably, the foam member 69 is formed of synthetic resin polymers such as polyurethane, and with a pore size between about 40 and 200 micron in maximum capillary openings.

More particularly, the foam member 69 may be treated with a Dow Corning ® antiwetting and antifoamer compound to further enhance defoaming and degassing ability of the member. Preferably, the foam member 69 is enclosed on both sides by a sock or woven cover 71 formed of synthetic polymeric threads. Good results are obtained where the cover 71 is formed of the Tricot ® filament of 140 Denier weave. The foam member 69 and cover 71 do not have a wick action to blood, and therefore the blood can not foam or reform into a gas bubble condition. The gas is released between the wall 59 and the foam member 69, and also within the member itself. The released gas migrates upwardly and eventually accumulates in the chamber 61 and the open zone of the blood reservoir 72. As a result, the blood leaves the foam member and cover to rest in the blood reservoir 72 at a level 73 from which it is removed and returned to the patient by the blood outlet 21 in a degassed and foam free state and at a proper certain temperature required in the medical procedure being practiced.

A nozzle 70 gives access to the reservoir 72 for drug introduction, priming purposes, or for other uses.

Although the cover 71 can be mounted about the foam member 69 in any desired manner, the cover as a sock can be returned upwardly on both sides of the member. The member 69 is secured in place by a snapping 74 held in an exterior circumferential groove 76 in the wall 59. The cover 71 passes in two layers 78 over the ring 74 and they are secured beneath a clamp ring 77 to the exterior surface of the wall 59 adjacent the conical inlet member 56.

The blood reservoir 72 is connected fluid wise to the outlet tube 62 so that released oxygen gas (and any other gases present in the blood) can be removed through the gas head 22. The head 22 is mounted on the cover 14 and the outlet tube 62 may be extended downwardly into a socket 79 formed in the conical inlet member 56. The head 22 has an outlet nozzle 79 which can be connected to a gas aspirating system so that the released oxygen and other gases are removed from the operating room area. For this purpose, the head 22 removes the gases from the outlet chamber 61 and reservoir 72 through the nozzle 79. In addition, the vessel 12 is maintained at substantially near atmospheric pressure by a vented shroud 81 that is carried on the head 22 to provide an atmospheric inlet chamber 82 that connects to the nozzle 79 through a perforated tube 83 that mounts the head 22 to the cover 14. There is a constant air flow from the atmosphere through the slotted tube 83 to intermix with the oxygen and other gases (nitrogen, anesthetic, etc.) released from the blood in the second stage 24. Therefore, the vessel 12 internally can never be at any substantially greater gas pressure that atmospheric which closely resembles the blood circulating condition in the human lungs. In addition, this combined atmospheric and vessel released gas removal protects the medical professionals from having to work in an environment containing anesthesia gases released by the patient through his blood being treated in the device 11.

The container 13 and cover 14, along with the several described internal components, can all be injection molded from the same transparent plastic materials except for the metal tube 37. The molded parts and tube can be provided with internested lips, grooves, offsets, etc. so the parts can readily be assembled by insertion into the container and then secured together by mounting of the cover into place. Naturally, subassembly of the wall 59, foam member 69 and cover 71 with rings 66, 74 and 77 are priorly made. A simple adhesive sealing of the cover to the container completes the assembly of the one use, disposable blood treatment devive 11. After assembly, the device 11 is sterilized (as by the gas ethylene oxide) and sealed into a sterile film package which may include the several hoses connected to the various inlet and outlet connections.

The device 11 has a unique first stage 19 with a highly efficient oxygenating feature and thin-film heat exchanging capability with blood-coolant in counter-current flow relationship. As a result, blood treatment in oxygenation and temperature adjustment are both highly efficient, accurate and safe to the patient. The second stage 24 produces high levels of defoaming and degassing of the blood to be returned to the patient with removal of the relayed gases while the vessel is at near atmospheric conditions. In addition to these advantages the device 11 is easily assembled from drawn metal and molded plastic parts to provide a sterile package, one use and disposal blood treatment apparatus.

From the foregoing, it will be apparent that there has been provided a novel device which provides proper and safe blood treatment in circulation conditions outside a patient. It will be appreciated that certain changes and alterations can be made in this device without departing from the spirit of this invention. These changes are contemplated by and are within the scope of the appended claims that define the invention. Additionally, the present description is intended to be taken as an illustration of this invention.

What is claimed is:

1. A blood oxygenator comprising:
 (a) a vessel molded from transparent plastics with an open-top lower container and having sealed thereto in a fluid (-) tight manner an enclosing cover;
 (b) said lower container having an integral upright cylindrical wall extending substantially the height thereof;
 (c) inlet means at the lower end of said cylindrical wall for directing upwardly a mixture of inflowing streams of blood and oxygen gas;
 (d) said inlet means including a porous member for dispersing finely divided oxygen gas bubbles into the blood stream;
 (e) said cylindrical wall carrying a plurality of inwardly directed vertical ribs;
 (f) a closed bottomed metal tube slideably mounted concentrically within said cylindrical wall, and said tube having outwardly directed flutes internested with said ribs for providing a plurality of upright thin film blood and oxygen flow channels between said cylindrical wall and said tube;
 (g) outlet means for removing the mixture of blood and oxygen gas from adjacent the upper end of said tube;
 (h) an insulative tubular member having an axial passageway mounted concentrically within said tube in laterally spaced relationship providing an annulus therebetween;
 (i) inlet means in said cover for inflowing a liquid coolant downwardly through said annulus of said tubular member;
 (j) outlet means in said cover for outflowing the coolant upwardly from said axial passageway of said tubular member;
 (k) a spacer supporting the lower end of said tubular member relative to the closed bottom of said tube for providing a fluid path between the inflowing and outflowing coolant;
 (l) a vent bypass port in said cover between the coolant inlet and outlet means whereby said annulus about said tubular member is completely filled;
 (m) an oblong mounting ring carried in the bottom of said lower container;
 (n) an oblong vertical perforated wall with an open top and a bottom end seated upon said mounting ring in fluid tight relationship;
 (o) said vertical perforated wall carrying a plurality of vertically elongated openings and a plurality of exterior vertical ribs between said elongated openings;
 (p) an open-pore foam member surrounding said vertical perforated wall and said foam member enclosed on its side surfaces by a woven cover formed of synthetic polymeric threads;
 (q) fing means sealing fluid tightly the top and bottom ends of said foam member to said vertical perforated wall;
 (r) a conical inlet member with an open central portion positioned above said vertical perforated wall to receive an inflow of the blood and oxygen mixture from said outlet means associated with said metal tube; and said conical inlet member;

(s) said conical inlet member directing the blood and oxygen mixture along the interior surface of said vertical perforated wall in a downward splash free flow;

(t) an upright semicylindrical flow diverter positioned on said conical inlet member for deflecting blood and gas mixture inflow from direct straight line passage into said conical inlet member;

(u) a blood reservoir surrounding said vertical perforated wall in said vessel for receiving degassed and defoamed blood traversing said foam member through said vertical elongated openings;

(v) said blood reservoir having a fluid connection with outlet means for the outflow from said vessel of degassed and foam free blood;

(w) said vertical perforated wall at its open top and said blood reservoir having a fluid connection with outlet means for the outflow from said vessel of free oxygen gas; and (x) said cover carrying projecting members for securely mounting the several elements (C-K) and (M-W) within said lower container.

2. The blood oxygenator of claim 1 wherein said cover has a downwardly projecting perforated sleeve in fluid connection with said vertical perforated wall at its open top and said blood reservoir, and said outlet means for removing the outflow of free oxygen gas including a projecting nozzle assembly having an open bottomed skirt for admitting aspirated air into the outflowing free oxygen gas.

3. The blood oxygenator of claim 1 wherein all interface surfaces between said cover and said lower container are on horizontal planes.

4. The blood oxygenator of claim 3 wherein said cover has an upright tubular neck to receive respectively a cup member providing for inlet and outlet means for inflowing and outflowing coolant, and said tubular neck and cup member being coaxially aligned with said axial passage of said insulative tubular member.

5. The blood oxygenator of claim 3 wherein said metal tube extends in an outward flared rectangular end and said flared tubular end is telescoped with said tubular neck and secured fixedly in place by said cup member.

6. The blood oxygenator of claim 5 wherein said outlet means for removing outflowing coolant includes a downwardly extending external shouldered pipe received in said axial passage at the upper end of said insulative tubular member.

* * * * *